(12) United States Patent
Fukuhara et al.

(10) Patent No.: US 9,700,885 B2
(45) Date of Patent: Jul. 11, 2017

(54) SPECIMEN CONCENTRATION CONTAINER AND SPECIMEN CONCENTRATING METHOD USING SAME

(71) Applicant: Panasonic Healthcare Holdings Co., Ltd., Tokyo (JP)

(72) Inventors: Takaomi Fukuhara, Ehime (JP); Toshifumi Nanjo, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 330 days.

(21) Appl. No.: 14/371,714

(22) PCT Filed: Dec. 27, 2012

(86) PCT No.: PCT/JP2012/008391
§ 371 (c)(1),
(2) Date: Jul. 10, 2014

(87) PCT Pub. No.: WO2013/105204
PCT Pub. Date: Jul. 18, 2013

(65) Prior Publication Data
US 2015/0011012 A1    Jan. 8, 2015

(30) Foreign Application Priority Data
Jan. 12, 2012 (JP) .................................. 2012-003722

(51) Int. Cl.
*B01L 3/00* (2006.01)
*G01N 1/40* (2006.01)

(52) U.S. Cl.
CPC ......... *B01L 3/5021* (2013.01); *B01L 3/50215* (2013.01); *G01N 1/4077* (2013.01);
(Continued)

(58) Field of Classification Search
CPC ...................................................... B01L 3/5021
(Continued)

(56) References Cited

U.S. PATENT DOCUMENTS 3,814,248 A * 6/1974 Lawhead ............ B01L 3/50215
                                                      210/117
4,214,993 A   7/1980 Forsythe, Jr. et al.
(Continued)

FOREIGN PATENT DOCUMENTS

CN    102301220 A    12/2011
JP    2003-021583 A    1/2003
(Continued)

OTHER PUBLICATIONS

Japanese Office Action dated Jul. 26, 2016 issued in Japanese Patent Application No. 2013-553113.
(Continued)

*Primary Examiner* — Christine T Mui
*Assistant Examiner* — Emily Berkeley
(74) *Attorney, Agent, or Firm* — McDermott Will & Emery LLP

(57) ABSTRACT

A specimen concentration container contains a specimen-containing liquid mixture, and the liquid mixture is concentrated in the specimen concentration container. The specimen concentration container includes: a tubular container main body including an upper surface on which an upper surface opening portion is formed; an upper surface opening portion communicating with an inside of the container main body; a specimen concentration portion formed at a bottom portion side of the container main body and containing the concentrated liquid mixture; and a specimen lid provided in the container main body and configured to cover the upper surface opening portion.

10 Claims, 7 Drawing Sheets

(52) U.S. Cl.
CPC . *B01L 2300/0851* (2013.01); *B01L 2400/049* (2013.01); *B01L 2400/0409* (2013.01); *B01L 2400/0616* (2013.01); *B01L 2400/0633* (2013.01); *G01N 2001/4083* (2013.01); *Y10T 436/25375* (2015.01)

(58) Field of Classification Search
USPC .......................................................... 436/177
See application file for complete search history.

(56) References Cited

U.S. PATENT DOCUMENTS

| | | | |
|---|---|---|---|
| 4,226,669 A | | 10/1980 | Vilardi |
| 4,698,311 A | | 10/1987 | Hall et al. |
| 4,990,129 A | | 2/1991 | Nielsen |
| 5,269,927 A | * | 12/1993 | Fiehler ................ B01L 3/50215 210/513 |
| 5,389,265 A | * | 2/1995 | Luoma, II ............ B01L 3/5021 210/745 |
| 5,484,734 A | | 1/1996 | Kimura |
| 5,785,925 A | | 7/1998 | U'Ren |
| 6,933,109 B2 | | 8/2005 | Anderson |
| 7,252,212 B2 | | 8/2007 | Anjanappa et al. |
| 8,535,945 B2 | | 9/2013 | Halverson |
| 2002/0081569 A1 | | 6/2002 | Anderson |
| 2002/0090729 A1 | | 7/2002 | Neeper et al. |
| 2003/0205538 A1 | | 11/2003 | Dorian |
| 2004/0067536 A1 | | 4/2004 | Haubert et al. |
| 2004/0071595 A1 | | 4/2004 | Neeper et al. |
| 2004/0256415 A1 | | 12/2004 | Anjanappa et al. |
| 2011/0250586 A1 | | 10/2011 | Halverson |
| 2013/0095007 A1 | | 4/2013 | Haubert et al. |

FOREIGN PATENT DOCUMENTS

| | | |
|---|---|---|
| JP | 2003-302319 A | 10/2003 |
| JP | 2003-531381 A | 10/2003 |
| JP | 2004-028819 A | 1/2004 |
| JP | 2005-524451 A | 8/2005 |
| JP | 2006-502389 A | 1/2006 |
| JP | 2009-145260 A | 7/2009 |
| JP | 2013-528785 A | 7/2013 |

OTHER PUBLICATIONS

Chinese Office Action dated Jun. 17, 2015 issued in Chinese Patent Application No. 201280066857.2.
Extended European Search Report dated May 19, 2015 in EP 12865157.7.
International Search Report issued in International Application No. PCT/JP2012/008391 mailed Mar. 12, 2013.

* cited by examiner

SPECIMEN CONCENTRATION CONTAINER AND SPECIMEN CONCENTRATING METHOD USING SAME

RELATED APPLICATIONS

This application is the U.S. National Phase under 35 U.S.C. §371 of International Application No. PCT/JP2012/008391, filed on Dec. 27, 2012, which in turn claims the benefit of Japanese Application No. 2012-003722, filed on Jan. 12, 2012, the disclosures of which are incorporated by reference herein.

TECHNICAL FIELD

The present invention relates to a specimen concentration container and a specimen concentrating method using the same.

BACKGROUND ART

According to a conventional method of collecting a specimen from a biological sample, first, a biological sample is obtained. Next, a liquid mixture prepared by mixing the biological sample and an extraction liquid is poured into a specimen concentration container. Then, the specimen concentration container is rotated by a centrifuge under reduced pressure, and centrifugal force is generated. Thus, a certain amount of concentrated liquid mixture is obtained (see PTL 1, for example).

CITATION LIST

Patent Literature

PTL 1: Japanese Laid-Open Patent Application Publication No. 2003-21583

SUMMARY OF INVENTION

Technical Problem

However, a problem of the above conventional art is that the work efficiency is low.

More specifically, a specimen concentration portion is provided at a bottom surface portion of a specimen concentration container disclosed in PTL 1. The specimen concentration portion is a narrow tube whose inner diameter is smaller than that of the other portion (a main body portion of the specimen concentration container).

To be specific, in a case when the specimen concentration container is rotated by a centrifuge under reduced pressure, the liquid mixture in the container main body vaporizes through an upper surface opening portion formed on an upper surface side of the container main body. With this, the liquid mixture in the container main body is concentrated.

When the amount of liquid mixture becomes a certain amount, the amount of specimens in the liquid mixture in this state is measured.

As described above, the specimen concentration portion having a narrow tube shape whose inner diameter is smaller than that of the container main body is provided at the bottom surface portion of the container main body of the conventional specimen concentration container. Therefore, when a liquid surface of the liquid mixture reaches the upper surface of the specimen concentration portion, the surface area of the liquid mixture that contacts air becomes drastically small, so that the vaporization amount of liquid mixture in the conventional specimen concentration container becomes drastically small.

As above, according to the specimen concentration container of the above conventional example, when the liquid surface of the liquid mixture reaches the specimen concentration portion, the subsequent vaporization amount becomes drastically small. Therefore, without observing the amount of liquid mixture at all times, a substantially constant amount of liquid mixture can be left in the specimen concentration portion.

However, even in a case where the specimen concentration portion is provided, the upper surface of the specimen concentration portion is open, so that if the liquid mixture is left for a long period of time, the liquid mixture surely vaporizes from the specimen concentration portion. As a result, a constant amount of liquid mixture cannot be left in the specimen concentration portion in some cases. Therefore, an operator has to observe the amount of liquid mixture in the container main body at all times or many times. Thus, the work efficiency is extremely low.

The present invention was made to solve the above problems, and an object of the present invention is to realize a specimen concentration container capable of improving the work efficiency.

Solution to Problem

To solve the above problems, a specimen concentration container according to the present invention is a specimen concentration container which contains a specimen-containing liquid mixture and in which the liquid mixture is concentrated, the specimen concentration container including: a tubular container main body including an upper surface on which a first opening portion is formed; a specimen concentration portion which includes a second opening portion communicating with an inside of the container main body, is formed at a bottom portion side of the container main body, and contains the concentrated liquid mixture; and a specimen lid provided in the container main body and configured to cover the second opening portion.

Advantageous Effects of Invention

The present invention is configured as above and has an effect of being able to improve the work efficiency.

DESCRIPTION OF EMBODIMENTS

Figure 1:
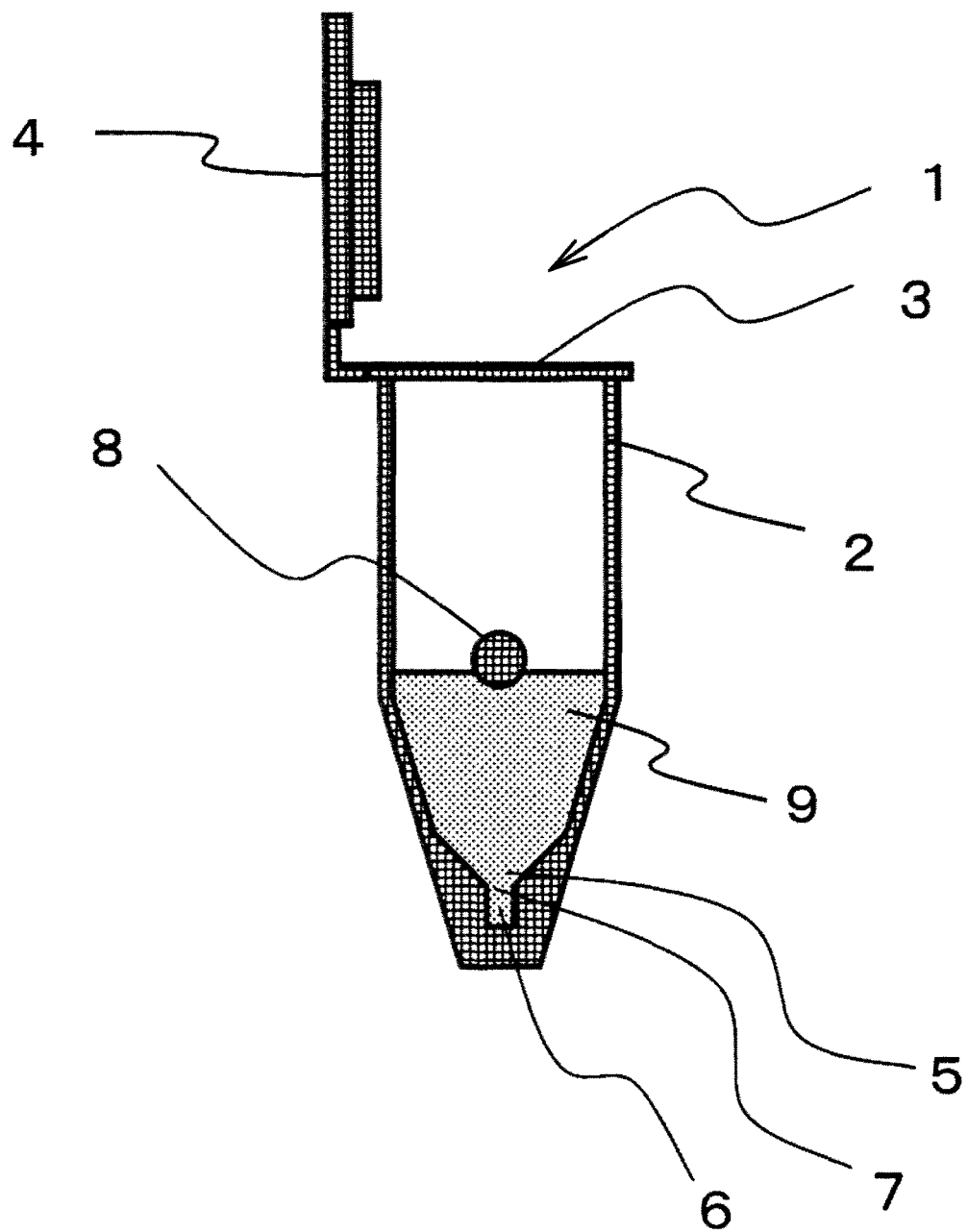
FIG. 1 is a cross-sectional view showing major components of a specimen concentration container according to Embodiment of the present invention.

The present invention provides the following aspects.

A specimen concentration container according to a first aspect of the present invention is a specimen concentration container which contains a specimen-containing liquid mixture and in which the liquid mixture is concentrated, the specimen concentration container including: a tubular container main body including an upper surface on which a first opening portion is formed; a specimen concentration portion which includes a second opening portion communicating with an inside of the container main body, is formed at a bottom portion side of the container main body, and contains the concentrated liquid mixture; and a specimen lid provided in the container main body and configured to cover the second opening portion.

According to the above configuration, since the specimen lid is included, it is possible to prevent a case where the concentrated liquid mixture contained in the specimen concentration portion vaporizes through the second opening portion and the first opening portion, and therefore, a constant amount of liquid mixture cannot be left in the specimen concentration portion. On this account, the operator does not have to observe the amount of liquid mixture in the specimen concentration portion. Thus, the specimen concentration container according to the first aspect of the present invention has an effect of being able to improve the work efficiency.

The specimen concentration container according to a second aspect of the present invention may be configured such that in the first aspect, an inner diameter of the second opening portion is smaller than that of the container main body, and the specimen concentration portion has a bottomed tubular shape including an upper portion on which the second opening portion is formed.

According to the above configuration, the specimen concentration portion has the bottomed tubular shape including the upper portion on which the second opening portion whose inner diameter is smaller than that of the container main body is formed, the vaporization amount of the liquid mixture can be reduced more in a case when the liquid surface of the liquid mixture is positioned in the specimen concentration portion than in a case where the liquid surface of the liquid mixture is positioned in the container main body. Since the specimen concentration portion has the bottomed tubular shape, the liquid mixture can be contained in the specimen concentration portion.

The specimen concentration container according to a third aspect of the present invention may be configured such that in the above first aspect or second aspect, when the liquid mixture is concentrated, and a liquid surface of the liquid mixture becomes lower than the second opening portion of the specimen concentration portion, the specimen lid covers the second opening portion.

According to the above configuration, when the liquid surface of the liquid mixture becomes lower than the second opening portion of the specimen concentration portion, the specimen lid can cover the second opening portion. To be specific, when the liquid mixture is contained only in the specimen concentration portion, the specimen lid can cover the second opening portion. Therefore, the liquid mixture contained in the specimen concentration portion can be prevented from vaporizing.

The specimen concentration container according to a fourth aspect of the present invention may be configured such that in any one of the first to third aspects, the specimen lid has a spherical shape having a diameter larger than that of the second opening portion. In a case where the specimen lid is formed in the spherical shape, any surface of the specimen lid can cover the second opening portion.

The specimen concentration container according to a fifth aspect of the present invention includes: a container main body whose upper surface is open; and a lid provided at an upper surface opening portion of the container main body so as to open or close the upper surface opening portion, wherein: a specimen concentration portion having a cup shape whose upper surface is open and whose inner diameter is smaller than that of the container main body is provided at an inner bottom surface portion of the container main body; and a specimen lid having a spherical shape whose diameter is larger than that of the upper surface opening portion of the specimen concentration portion is movably arranged on the upper surface opening portion of the specimen concentration portion.

According to the above configuration, since the lid is included, the specimen lid and the like in the container main body can be prevented from jumping out of the container main body. The specimen lid is placed on or above the upper surface opening portion of the specimen concentration portion having a cup shape. Therefore, when the specimen lid moves so as to cover the upper surface opening portion, the specimen lid can close the upper surface opening of the specimen concentration portion. On this account, for example, the specimen-containing liquid mixture contained in the specimen concentration portion can be prevented from being discharged by vaporization.

The specimen concentration container according to a sixth aspect of the present invention may be configured such that in any one of the first to fifth aspects, the specimen lid is made of synthetic resin.

The specimen concentration container according to a seventh aspect of the present invention may be configured such that in any one of the first to sixth aspects, the specimen lid is made of polypropylene resin.

The specimen concentration container according to an eighth aspect of the present invention may be configured such that in any one of the first to seventh aspects, the specimen lid is made of polyethylene resin.

The specimen concentration container according to a ninth aspect of the present invention may be configured such that in any one of the first to fifth aspects, the specimen lid is configured to float on the liquid mixture.

According to the above configuration, the specimen lid is configured to float on the liquid mixture. Therefore, when the liquid mixture contained in the specimen concentration container gradually vaporizes by concentration, and the liquid mixture is then contained only in the specimen concentration portion, the specimen lid can close the second opening portion that is the upper surface opening portion of the specimen concentration portion. On this account, the liquid mixture in the specimen concentration portion can be prevented from vaporizing, and a constant amount of liquid mixture can be left in the specimen concentration portion.

The specimen concentration container according to a tenth aspect of the present invention may be configured such that in the third aspect, when the liquid mixture is concentrated, and a liquid surface of the liquid mixture becomes lower than the second opening portion of the specimen concentration portion, the specimen lid surface-contacts the container main body in the vicinity of the second opening portion to cover the second opening portion.

According to the above configuration, the specimen lid surface-contacts the container main body in the vicinity of the second opening portion to cover the second opening portion. Therefore, the specimen lid can firmly close the second opening portion to prevent the liquid mixture in the specimen concentration portion from vaporizing.

The specimen concentration container according to an eleventh aspect of the present invention may be configured such that in the ninth or tenth aspect, the specimen lid includes therein a hollow portion. Since the specimen lid includes the hollow portion, the specific gravity of the specimen lid can be made lower than that of the liquid mixture. Therefore, the specimen lid can be caused to suitably float on the liquid mixture.

The specimen concentration container according to a twelfth aspect of the present invention may be configured such that in the ninth or tenth aspect, the specimen lid includes a columnar projecting portion projecting in one direction.

The specimen concentration container according to a thirteenth aspect of the present invention may be configured such that in the twelfth aspect, an entire length of the specimen lid including the projecting portion is longer than an inner diameter of the container main body.

Therefore, if the projecting portion of the specimen lid tries to move so as to flip upside down, the projecting portion contacts the inner peripheral surface of the container main body, so that the specimen lid is prevented from flipping upside down.

The specimen concentration container according to a fourteenth aspect of the present invention may be configured such that in the twelfth aspect, the specimen lid includes a specimen lid main body on which the projecting portion is formed, the specimen lid main body including a surface that closes the second opening portion, and at least an inside of the projecting portion is hollow.

According to the above configuration, since the inside of the projecting portion is hollow, the center of gravity of the specimen lid can be set at the specimen lid main body side. Therefore, the specimen lid can be arranged in the container main body of the specimen concentration container such that the specimen lid main body faces downward, and the projecting portion faces upward. On this account, a surface of the specimen lid main body of the specimen lid can cover the second opening portion, the surface being located opposite to the projecting portion.

A specimen concentrating method according to a fifteenth aspect of the present invention is a specimen concentrating method using the specimen concentration container according to any one of the first to fourteenth aspects and includes: arranging in the specimen concentration container the liquid mixture prepared by mixing the extraction liquid and a specimen; rotating the specimen concentration container by a centrifuge under reduced pressure; and generating centrifugal force to concentrate the liquid mixture.

According to the above method, since the specimen concentration container that is rotated by the centrifuge includes the specimen lid, it is possible to prevent a case where the concentrated liquid mixture contained in the specimen concentration portion vaporizes through the second opening portion and the first opening portion, and therefore, a constant amount of liquid mixture cannot be left in the specimen concentration portion. On this account, the operator does not have to observe the amount of liquid mixture in the specimen concentration portion. Thus, the specimen concentrating method according to the fifteenth aspect of the present invention has an effect of being able to improve the work efficiency.

Hereinafter, one embodiment of the present invention will be explained in detail in reference to the drawings.

Embodiment

As shown in FIG. 1, a specimen concentration container 1 of the present embodiment is, for example, a container which contains a liquid mixture prepared by mixing a specimen of a biological sample or the like and an extraction liquid and in which the liquid mixture is concentrated. The specimen concentration container 1 includes: a container main body 2 having an upper surface opening portion (first opening portion) 3; and a lid 4 provided at the upper surface opening portion 3 of the container main body 2 so as to open or close the upper surface opening portion 3. FIG. 1 is a cross-sectional view showing major components of the specimen concentration container 1 according to Embodiment of the present invention.

A specimen concentration portion 6 is formed under an inner bottom surface portion 5 of the container main body 2. The specimen concentration portion 6 includes an upper surface having an upper surface opening portion (second opening portion) 7 communicating with the inside of the container main body 2 and is formed in a cup shape (bottomed tubular shape) whose inner diameter is smaller than that of the container main body 2. The specimen concentration portion 6 contains the concentrated liquid mixture.

The container main body 2 is a tubular member configured such that an inner peripheral surface area (cut surface area) thereof decreases in a stepwise fashion in a direction from an upper surface thereof toward a bottom surface thereof. More specifically, as shown in FIG. 1, regarding the shape of the inside of the container main body 2, a straight portion having a constant inner peripheral surface area (corresponding to the inner peripheral surface area of the upper surface opening portion 3) is formed at a predetermined section extending from the upper surface toward the bottom surface. Then, a tapered portion whose inner peripheral surface area (cut surface area) gradually decreases is formed next to the straight portion formed at the predetermined section. The tapered portion is formed such that: the inner peripheral surface area (cut surface area) thereof decreases at a constant rate; and from a certain portion thereof, the inner peripheral surface area (cut surface area) thereof decreases at a rate higher than the constant rate. The specimen concentration portion 6 is formed under the tapered portion and at the bottom surface side of the container main body 2. The specimen concentration portion 6 has a cup shape (bottomed tubular shape) having a constant inner peripheral surface area (the inner peripheral surface area of the specimen concentration portion 6).

A specimen lid 8 is movably provided in the container main body 2 to be located on or above the upper surface opening portion 7 of the specimen concentration portion 6. The specimen lid 8 has a spherical shape having a diameter larger than that of the upper surface opening portion 7 of the specimen concentration portion 6. To completely prevent the concentrated specimen from leaking, the bottom surface and side surface of the specimen concentration portion 6 are covered with resin or the like.

The specimen lid 8 is made of a material, such as synthetic resin, which is lower in specific gravity than water and is made of PP (polypropylene) resin, PE (polyethylene) resin or the like. To be specific, the specimen lid 8 may be made of a material that floats on a liquid mixture 9 prepared by mixing the extraction liquid and the specimen.

When the liquid mixture 9 vaporizes, and the liquid surface thereof lowers to the position of the upper surface opening portion 7 of the specimen concentration portion 6, the specimen concentration portion 6 is closed by the specimen lid 8 having the spherical shape whose diameter is larger than that of the upper surface opening portion 7 of the specimen concentration portion 6 and smaller than the inner diameter (cut surface diameter) of the upper surface opening portion 3 of the container main body 2.

The lid 4 is provided at the container main body 2 so as to open or close the upper surface opening portion 3. The container main body 2 can be sealed by closing the lid 4.

As above, since the lid 4 closes the upper surface opening portion 3 of the container main body 2, the specimen lid 8 can be prevented from jumping out of the specimen concentration container 1 during transportation or the like. After the extraction liquid or the liquid mixture prepared by mixing the extraction liquid and the specimen is poured into the container main body 2, the lid 4 closes the upper surface opening portion 3 of the container main body 2, so that the extraction liquid, the liquid mixture, or the like can be prevented from spilling out through the upper surface opening portion 3.

Example in which the specimen is concentrated by using the specimen concentration container 1 configured as above will be explained in reference to FIGS. 1 to 5.

As shown in FIG. 1, the liquid mixture 9 prepared by mixing the extraction liquid and the specimen is contained in the specimen concentration container 1. In a state where the liquid mixture 9 is contained in the specimen concentration container 1, the specimen lid 8 floats on the liquid surface of the liquid mixture 9. This is because the specimen lid 8 having the spherical shape is lower in specific gravity than the liquid mixture 9.

Figure 2:
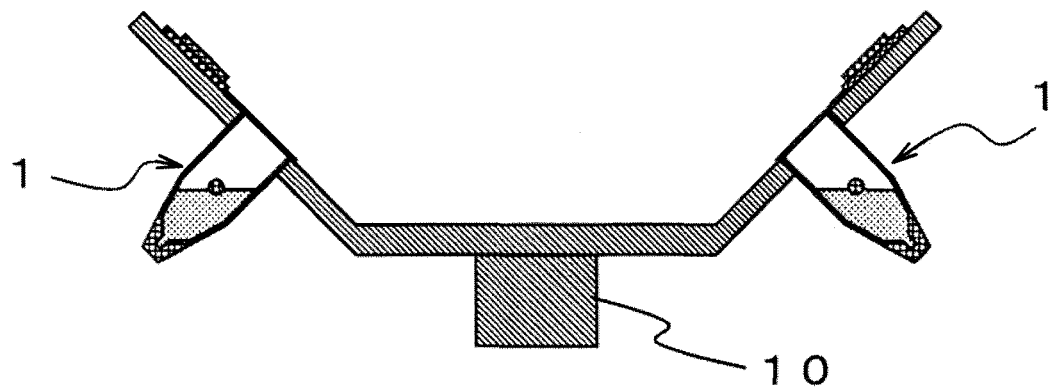
FIG. 2 is a cross-sectional view showing one example of a specimen concentrating method using the specimen concentration container shown in FIG. 1.
Figure 3:
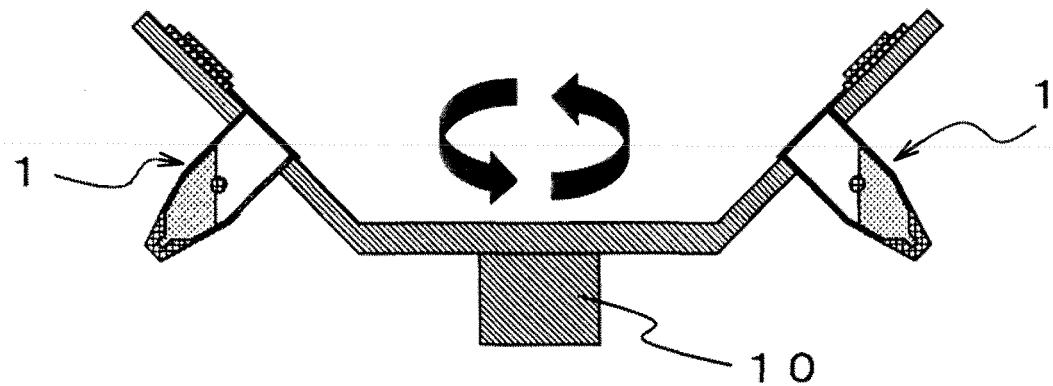
FIG. 3 is a cross-sectional view showing one example of the specimen concentrating method using the specimen concentration container shown in FIG. 1.

Next, as shown in FIG. 2, the specimen concentration container 1 is placed at a centrifugal rotating device 10. Then, as shown in FIG. 3, the pressure in the specimen concentration container 1 is reduced while causing the specimen concentration container 1 to rotate by the centrifugal rotating device 10 at high speed. FIGS. 2 and 3 are cross-sectional views each showing one example of the specimen concentrating method using the specimen concentration container 1 shown in FIG. 1. FIG. 2 shows a state where the specimen concentration container 1 is placed at the centrifugal rotating device 10. FIG. 3 shows a state where the specimen concentration container 1 placed at the centrifugal rotating device 10 is rotated.

Figure 4:
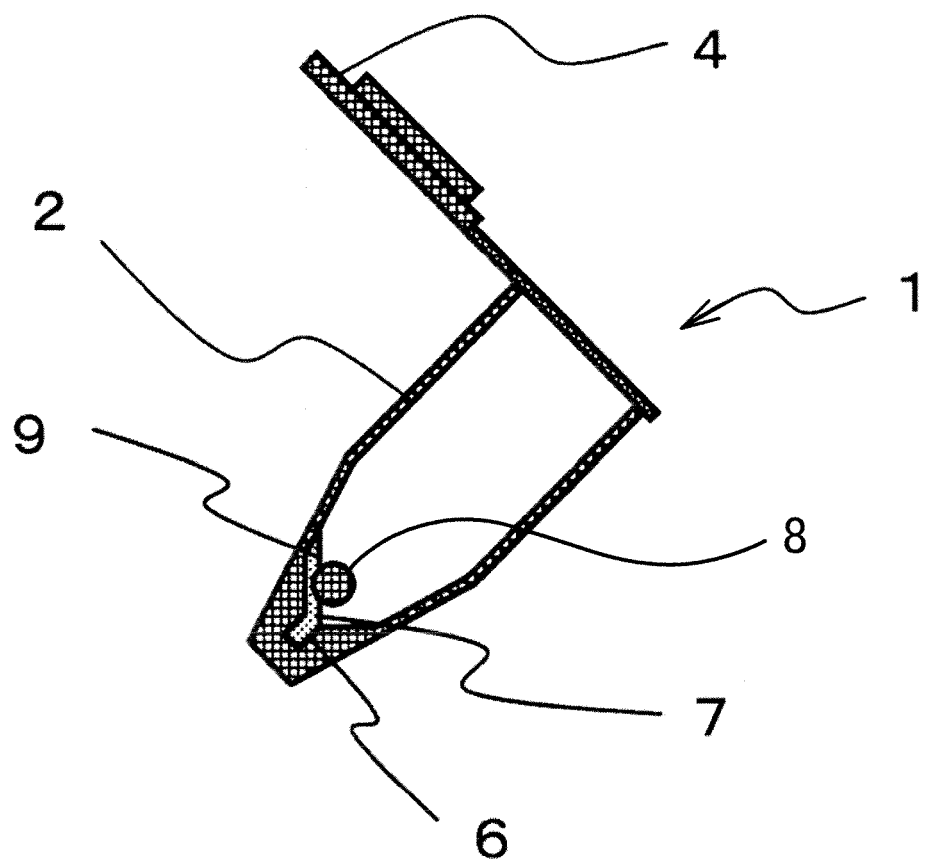
FIG. 4 is a cross-sectional view showing one example of the specimen concentrating method using the specimen concentration container shown in FIG. 1.

Since the pressure is reduced by the above operation, the boiling point of the liquid mixture 9 lowers, and the liquid mixture 9 in the container main body 2 decreases by vaporization. Thus, as shown in FIG. 4, the liquid surface of the liquid mixture 9 gets close to the position of the upper surface opening portion 7 of the specimen concentration portion 6. FIG. 4 is a cross-sectional view showing one example of the specimen concentrating method using the specimen concentration container 1 shown in FIG. 1. FIG. 4 schematically shows a position of the liquid surface of the liquid mixture 9 that has been partially vaporized and a positional relation between the specimen concentration portion 6 and the specimen lid 8.

Figure 5:
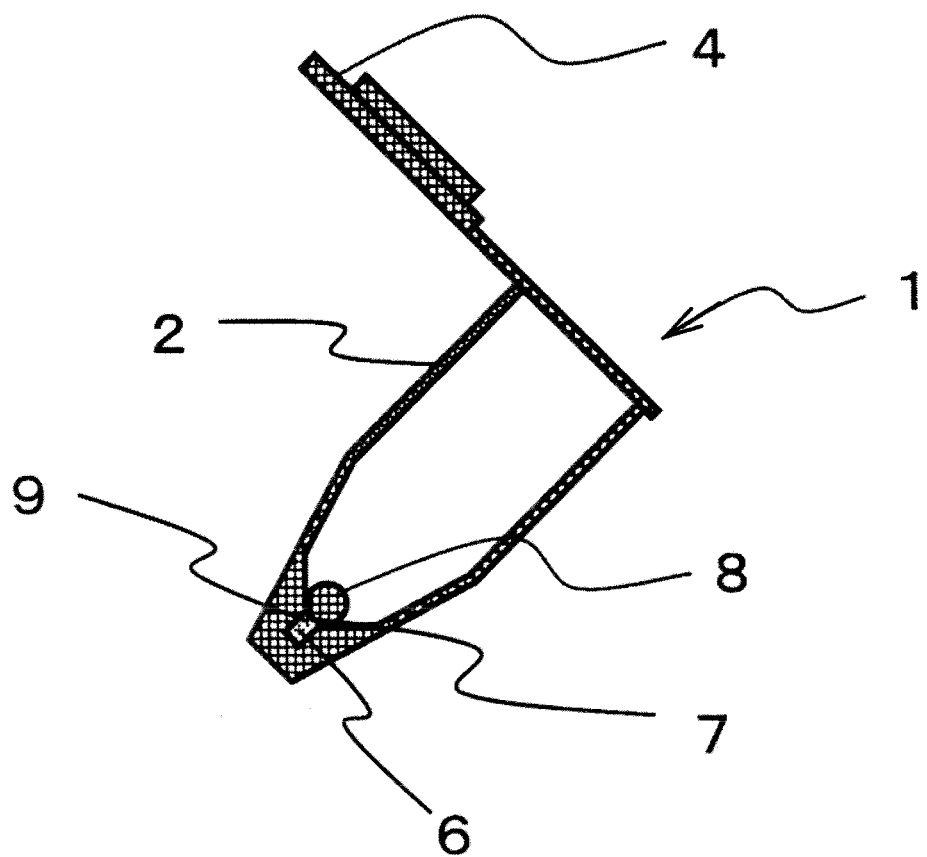
FIG. 5 is a cross-sectional view showing one example of the specimen concentrating method using the specimen concentration container shown in FIG. 1.

By continuing the operation shown in FIG. 3, the liquid mixture 9 in the container main body 2 gradually decreases due to vaporization as shown in FIG. 5. FIG. 5 is a cross-sectional view showing one example of the specimen concentrating method using the specimen concentration container 1 shown in FIG. 1. FIG. 5 schematically shows the position of the liquid surface of the liquid mixture 9 that has been partially vaporized and the positional relation between the specimen concentration portion 6 and the specimen lid 8. Here, the specimen lid 8 having the spherical shape whose diameter is larger than that of the upper surface opening portion 7 of the specimen concentration portion 6 is movably placed on the upper surface opening portion 7 of the specimen concentration portion 6 in the container main body 2 of the specimen concentration container 1. Here, as shown in FIG. 5, when the liquid surface of the liquid mixture 9 becomes lower than the position of the upper surface opening portion 7 of the specimen concentration portion 6, the upper surface opening portion 7 of the specimen concentration portion 6 is covered with the specimen lid 8.

Therefore, for example, even if the rotation of the centrifugal rotating device 10 under reduced pressure is continued after the upper surface opening portion 7 of the specimen concentration portion 6 is covered with the specimen lid 8, the liquid mixture 9 in the specimen concentration portion 6 decreases little by vaporization.

To be specific, in the present embodiment, even if the rotation of the centrifugal rotating device 10 under reduced pressure is continued, the liquid mixture 9 decreases little by vaporization. Therefore, the operator does not have to observe the amount of liquid mixture in the container main body at all times or many times, and a constant amount of concentrated liquid mixture 9 can be obtained. Thus, the work efficiency is extremely high.

Modification Example

Figure 6:
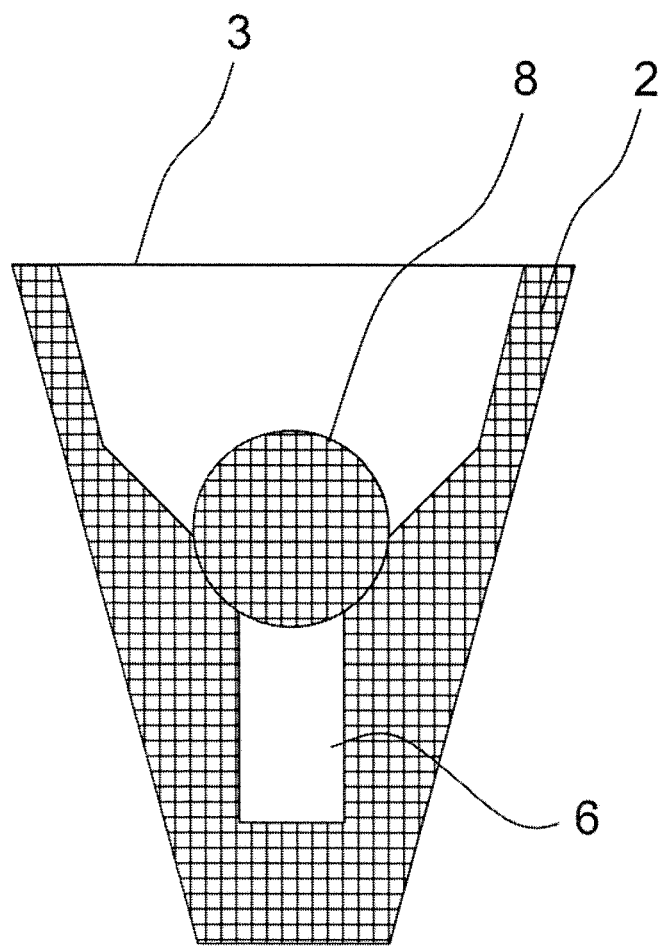
FIG. 6 is a cross-sectional view showing the specimen concentration container according to Modification Example of Embodiment of the present invention.

As described above, the container main body 2 of the specimen concentration container 1 according to the present embodiment is configured such that the specimen concentration portion 6 having the bottomed tubular shape is formed next to the tapered portion. However, to improve a sealing degree of the upper surface opening portion 7 of the specimen concentration portion 6 by the specimen lid 8, the tapered portion in the vicinity of the upper surface opening portion 7 may be depressed in an arc shape so as to correspond to an outer shape of the specimen lid 8 as shown in FIG. 6. FIG. 6 is a cross-sectional view of the specimen concentration container 1 according to Modification Example of Embodiment of the present invention. FIG. 6 shows a cross-sectional shape of the container main body 2 in the vicinity of the upper surface opening portion 7 of the specimen concentration portion 6.

To be specific, in order that the specimen lid 8 stably serves as a lid of the specimen concentration portion 6, it is advantageous to cause the shape of a predetermined portion (especially a portion in the vicinity of the upper surface opening portion 7 of the specimen concentration portion 6) of the container main body 2 to correspond to the outer shape of the specimen lid 8. As above, by causing the shape of the predetermined portion of the container main body 1 to correspond to the outer shape of the specimen lid 8, the sealing degree at the specimen concentration portion 6 can be further improved. Therefore, the vaporization amount of the liquid mixture can be further reduced. Especially, as a contact area between the specimen lid 8 and the container main body 2 increases in a state when the liquid surface of the liquid mixture 9 is lower in position than the upper surface opening portion 7 of the specimen concentration portion 6, the effect of reducing the vaporization amount of the liquid mixture 9 increases.

Figure 7:
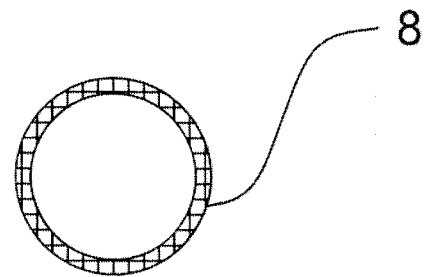
FIG. 7 is a cross-sectional view showing the schematic configuration of a specimen lid according to Modification Example of Embodiment of the present invention.
Figure 8:
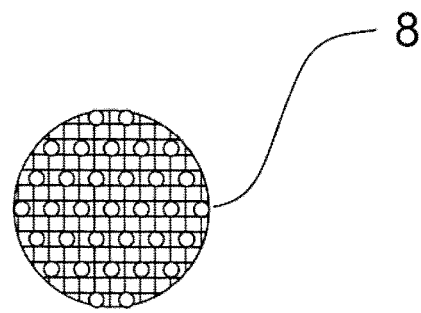
FIG. 8 is a cross-sectional view showing the schematic configuration of the specimen lid according to Modification Example of Embodiment of the present invention.

The foregoing has explain an example in which the specimen lid 8 has the spherical shape. However, the shape of the specimen lid 8 according to the present embodiment is not limited to the simple spherical shape. Specifically, as shown in FIGS. 7 and 8, a hollow portion may be formed in the specimen lid 8. For example, as shown in FIG. 7, the inside of the specimen lid 8 may be hollow. In addition, as shown in FIG. 8, a plurality of small spherical hollow portions (such as air bubbles) may be formed in the specimen lid 8. FIGS. 7 and 8 are cross-sectional views each showing the schematic configuration of the specimen lid 8 according to Modification Example of the present embodiment By forming the hollow portion in the specimen lid 8 as with the specimen lid 8 shown in FIG. 7 or 8, the specific gravity of the entire specimen lid 8 can be reduced. With this, even if the liquid mixture 9 is lower in specific gravity than water, the specimen lid 8 can serve as a floating lid that floats on the liquid surface of the liquid mixture 9.

Figure 9:
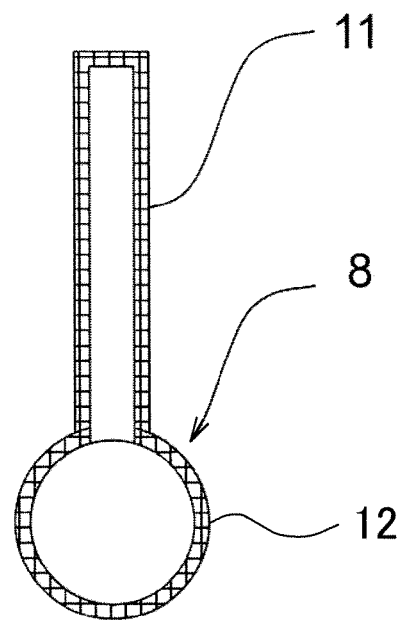
FIG. 9 is a cross-sectional view showing the schematic configuration of the specimen lid according to Modification Example of Embodiment of the present invention.
Figure 10:
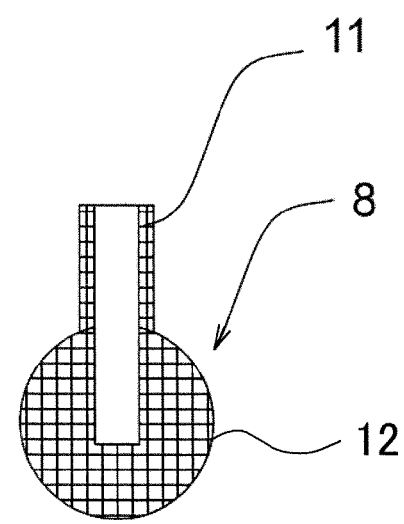
FIG. 10 is a cross-sectional view showing the schematic configuration of the specimen lid according to Modification Example of Embodiment of the present invention.

As shown in FIGS. 9 and 10, the specimen lid 8 may include a projecting portion 11. FIGS. 9 and 10 are cross-sectional views each showing the schematic configuration of the specimen lid 8 according to Modification Example of the present embodiment. The projecting portion 11 of the specimen lid 8 shown in each of FIGS. 9 and 10 is a rod-shaped member extending in one direction from a specimen lid main body 12 formed as a spherical portion of the specimen lid 8.

Here, the specimen lid 8 shown in FIG. 9 is defined such that the total of the length of the projecting portion 11 and the length of the spherical portion of the specimen lid main body 12, that is, the entire length of the specimen lid 8 including the projecting portion 11 is longer than a longest inner diameter of the container main body 2. Since the specimen lid 8 includes the projecting portion 11 as above, it is possible to prevent a case where the projecting portion 11 contacts the inner peripheral surface of the container main body 2, and the specimen lid 8 in the specimen concentration container 1 flips upside down.

Therefore, a predetermined surface of the specimen lid 8 can be located at the upper surface opening portion 7 side of the specimen concentration portion 6 at all times. Specifically, the specimen lid 8 shown in FIG. 9 can be arranged such that a spherical surface of the specimen lid main body 12 faces downward, and the projecting portion 11 faces upward. The specimen lid 8 can seal the upper surface opening portion 7 of the specimen concentration portion 6 by a predetermined spherical portion thereof at a predetermined timing. The inside of the specimen lid 8 may be entirely hollow as shown in FIG. 9.

As shown in FIG. 10, the specimen lid 8 may include the projecting portion 11 that is shorter than the projecting portion 11 of the specimen lid 8 shown in FIG. 9 and may include a columnar hollow portion extending from a tip end of the projecting portion 11 to a substantially center position of the specimen lid main body 12. Since the projecting portion 11 side is hollow as above, the center of gravity of the entire specimen lid 8 can be set at the specimen lid main body 8 side.

Therefore, when the specimen concentration container 1 is set at the centrifugal rotating device 10, and the centrifugal force is applied to the specimen concentration container 1, the specimen lid 8 is surely arranged such that the spherical surface of the specimen lid main body 12 faces downward, and the projecting portion 11 faces upward. The specimen lid 8 can seal the upper surface opening portion 7 of the specimen concentration portion 6 by the predetermined spherical portion thereof at the predetermined timing.

The specimen lid 8 is made of PP (polypropylene) resin, PE (polyethylene) resin, or the like. However, the material of the specimen lid 8 is not limited to these. For example, instead of a hard material, such as PP (polypropylene) resin or PE (polyethylene) resin, the specimen lid 8 may be made of resin having elasticity, such as synthetic rubber. In a case where the specimen lid 8 is made of the resin having elasticity, the degree of contact between the specimen lid 8 and the container main body 2 in the vicinity of the upper surface opening portion 7 of the specimen concentration portion 6 can be improved. Therefore, the vaporization of the liquid mixture 9 in the specimen concentration portion 6 can be effectively prevented. On this account, even in the case of using the liquid mixture 9 having high volatility, a constant amount of liquid mixture can be left in the specimen concentration portion.

INDUSTRIAL APPLICABILITY

As above, the present invention includes: a container main body whose upper surface is open; and a lid provided at an upper surface opening portion of the container main body so as to open or close the upper surface opening portion, wherein: a specimen concentration portion having a cup shape whose upper surface is open and whose inner diameter is smaller than that of the container main body is provided at an inner bottom surface portion of the container main body; and a specimen lid having a spherical shape whose diameter is larger than that of the upper surface opening portion of the specimen concentration portion is movably arranged on the upper surface opening portion of the specimen concentration portion. For example, the present invention is effective in a concentration treatment performed by utilizing a specimen concentration container, such as a Kuderna-Danish concentrator.

Therefore, the present invention is expected to be utilized as a specimen concentration container.

REFERENCE SIGNS LIST 1 specimen concentration container
2 container main body
3 upper surface opening portion
4 lid
5 inner bottom surface portion
6 specimen concentration portion
7 upper surface opening portion
8 specimen lid
9 liquid mixture
10 centrifugal rotating device
11 projecting portion
12 specimen lid main body

The invention claimed is:

1. A specimen concentration container comprising:
   a container main body having an upper surface on which a first opening portion is formed;
   a specimen concentration portion having a cup shape having an upper surface on which a second opening portion is formed and whose inner diameter is smaller than that of the container main body, the specimen concentration portion is provided at an inner bottom surface portion of the container main body; and a specimen lid having a spherical shape whose diameter is larger than that of the second opening portion of the specimen concentration portion and is smaller than an inner diameter of the container main body, and the specimen lid is movably arranged on the second opening portion of the specimen concentration portion, the specimen lid is configured to float on a liquid mixture within the container and cover the second opening portion when the specimen concentration container is rotated under reduced pressure.

2. The specimen concentration container according to claim 1, wherein the specimen lid is made of synthetic resin.

3. The specimen concentration container according to claim 1, wherein the specimen lid is made of polypropylene resin.

4. The specimen concentration container according to claim 1, wherein the specimen lid is made of polyethylene resin.

5. The specimen concentration container according to claim 1, wherein the specimen lid is configured to float on the liquid mixture.

6. The specimen concentration container according to claim 5, wherein the specimen lid includes therein a hollow portion.

7. The specimen concentration container according to claim 5, wherein the specimen lid includes a columnar projecting portion projecting in one direction.

8. The specimen concentration container according to claim 7, wherein an entire length of the specimen lid including the projecting portion is longer than an inner diameter of the container main body.

9. The specimen concentration container according to claim 1, wherein a body lid is provided at the first opening portion of the container main body so as to open or close the first opening portion.

10. A specimen concentrating method using the specimen concentration container according to claim 1, comprising:
arranging in the specimen concentration container the liquid mixture prepared by mixing the extraction liquid and a specimen;
evaporating a moisture in the liquid mixture;
rotating the specimen concentration container by a centrifuge under reduced pressure; and
sealing the specimen concentration portion by covering the second opening portion by a surface-contacting between the specimen lid and the container main body in the vicinity of the second opening portion to cover the second opening portion when an amount of the liquid mixture is reduced by evaporating and a liquid surface of the liquid mixture becomes lower than the second opening portion of the specimen concentration portion, wherein the specimen lid is configured to float on the liquid mixture.

* * * * *